(12) United States Patent
Saia et al.

(10) Patent No.: US 9,155,713 B2
(45) Date of Patent: Oct. 13, 2015

(54) METHOD AND APPARATUS FOR ALCOHOL ADMINISTRATION AND THERAPEUTIC TREATMENTS USING SAME

(71) Applicants: Mark Stephen Saia, Rohnert Park, CA (US); Michael J. Saia, Yuba City, CA (US)

(72) Inventors: Mark Stephen Saia, Rohnert Park, CA (US); Michael J. Saia, Yuba City, CA (US)

( * ) Notice: Subject to any disclaimer, the term of this patent is extended or adjusted under 35 U.S.C. 154(b) by 38 days.

(21) Appl. No.: 13/887,259

(22) Filed: May 3, 2013

(65) Prior Publication Data
US 2013/0245577 A1    Sep. 19, 2013

Related U.S. Application Data

(63) Continuation-in-part of application No. 13/412,355, filed on Mar. 5, 2012, now abandoned.

(51) Int. Cl.
*A61K 31/045* (2006.01)
*A61K 9/70* (2006.01)

(52) U.S. Cl.
CPC ............ *A61K 9/7084* (2013.01); *A61K 31/045* (2013.01)

(58) Field of Classification Search
CPC .. A61K 9/7084; A61K 9/7023; A61K 31/045
See application file for complete search history.

(56) References Cited

U.S. PATENT DOCUMENTS

| 4,764,379 | A | * | 8/1988 | Sanders et al. | 424/449 |
| 5,899,856 | A | * | 5/1999 | Schoendorfer et al. | 600/362 |
| 6,328,992 | B1 | * | 12/2001 | Brooke et al. | 424/449 |
| 6,974,588 | B1 | * | 12/2005 | Miranda et al. | 424/448 |

OTHER PUBLICATIONS

Carlsson, S.; Hammar, N.; Grill, V.; Kaprio, J. Alcohol Consumption and the Incidence of Type 2 Diabetes. A 20-year follow-up of the Finnish Twin Cohort Study. Diabetes Care, vol. 26, No. 10, Oct. 2003, p. 2785-2790.*

* cited by examiner

*Primary Examiner* — Susan Tran
*Assistant Examiner* — Jessica Worsham
(74) *Attorney, Agent, or Firm* — Larry D. Johnson

(57) ABSTRACT

The present invention provides a method and apparatus for the administration of alcohol to a person, and therapeutic treatments utilizing the method and apparatus. The invention provides an alcohol "patch" in the form of an adhesive patch or bandage-like structure bearing a quantity of alcohol for transdermal delivery to the user. Permeation enhancers, either chemical or structural, may be included to facilitate the penetration of the alcohol through the skin, and for increased efficacy of delivery of the alcohol to the bloodstream of the user.

7 Claims, 1 Drawing Sheet

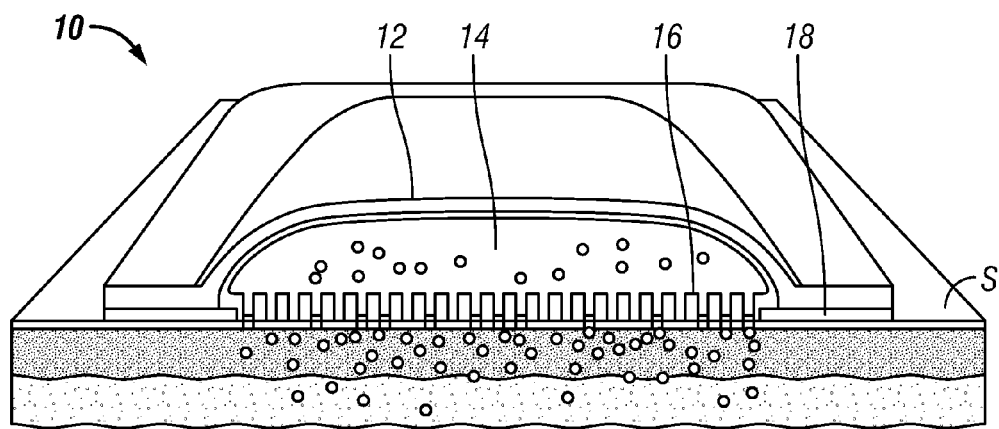

METHOD AND APPARATUS FOR ALCOHOL ADMINISTRATION AND THERAPEUTIC TREATMENTS USING SAME

CROSS REFERENCE TO RELATED APPLICATIONS

The present application is a continuation-in-part of application U.S. Ser. No. 13/412,355, filed Mar. 5, 2012, which claims priority to U.S. Provisional Patent Application Ser. No. 61/448,731, filed Mar. 3, 2011. The foregoing applications are incorporated by reference in their entirety as if fully set forth herein.

STATEMENT REGARDING FEDERALLY SPONSORED RESEARCH OR DEVELOPMENT

Not applicable.

REFERENCE TO A MICROFICHE APPENDIX

Not applicable.

TECHNICAL FIELD

The present invention relates generally to alcoholic beverages and alcohol consumption, and more particularly to an improved method and apparatus for the administration of alcohol to a person, and therapeutic treatments utilizing the method and apparatus.

BACKGROUND INFORMATION AND DISCUSSION OF RELATED ART

U.S. Pat. No. 4,764,379 to Sanders, et al. discloses a transdermal drug delivery device with dual permeation enhancers. A dosage form coadministers a drug and two percutaneous adsorption enhancers to a defined area of the skin. The dosage form comprises a body that contains supplies of drug and enhancers and has a basal surface that contacts the area of skin and transmits the drug and enhancers to the area for absorption thereby.

U.S. Pat. No. 4,804,541 to Nichols discloses a method, composition, and article for use in transdermal or percutaneous administration to humans of systemically active medicaments in the form of a solution in benzyl alcohol.

U.S. Pat. No. 5,899,856 to Schoendorfer, et al. describes a dermal patch detecting long-term alcohol consumption and method of use. A non-occlusive dermal patch for collecting vapor phase perspiration from a subject's skin and retaining an analyte such as ethanol in the perspiration is disclosed. In addition, a method of collecting vapor phase perspiration containing an analyte such as ethanol over a period up to several days and detecting the analyte to determine the wearer's consumption of the analyte during the period when the patch was worn is disclosed.

U.S. Pat. No. 5,948,433 to Burton, et al. teaches transdermal patches, including a backing layer, a liner layer, and a monolithic adhesive and drug-containing layer between the backing layer and the liner layer. The drug-containing adhesive layer includes polyisobutylene, a plasticizer for the polyisobutylene in which the ratio of the plasticizer and the polyisobutylene is less than about 0.8 and at least 5% of a filler. The drug so utilized is moderately soluble in the plasticizer.

U.S. Pat. No. 6,328,992 to Brooke, et al. discloses a Cannabinoid patch and method for cannabis transdermal delivery. A transdermal structure is provided for delivering cannabis chemical(s) to one's bloodstream. The structure comprises a backing layer which carries the cannabis chemical(s). The chemicals are contained in a film on the backing layer or within a cavity formed in the backing layer. Alternatively, an opening in a secondary layer that overlies the backing layer may be used to create the cavity. The structure is applied to one's skin so that the cannabis chemicals are in contact with the skin. A polymer material which is mixed with the cannabis and placed in the cavity or a membrane over the cavity may be used to control the flow of cannabis chemical(s) into the bloodstream. In an alternative embodiment, a porous material impregnated with cannabis chemical(s) may be used to hold the chemical(s) in the cavity. Because of the relatively slow transdermal flow rate of cannabis materials, it is preferred to utilize permeation enhancers in conjunction with the cannabis carrier or reservoir matrixes or skin contacting adhesive layers.

U.S. Pat. No. 6,974,588 to Miranda, et al. describes a transdermal patch for administering a volatile liquid drug, such as nicotine, transdermally to a patient comprising a four-layer laminated composite of: a top drug impermeable backing layer; a pressure sensitive silicone adhesive layer containing the drug; a pressure sensitive acrylic adhesive layer also containing the drug; and a removable siliconized release liner layer. Also disclosed is a method for treating a person for nicotine dependence and particularly for treating a woman for nicotine dependence.

U.S. Pat. No. 7,611,481 to Cleary, et al. teaches a dermal, transdermal, mucosal or transmucosal delivery device includes a backing layer overlying an ingredient containing reservoir, and having a microprotrusion array attached thereto, a cover for the reservoir having at least one opening therethrough, an adhesive layer and a liner layer. Upon removal of the liner layer, the device may be placed over the desired area of the skin or mucosa and adhesively applied thereto allowing the ingredients to flow from the reservoir through the at least one opening to the skin or mucosa.

The foregoing patents reflect the current state of the art of which the present inventor is aware. Reference to, and discussion of, these patents is intended to aid in discharging Applicant's acknowledged duty of candor in disclosing information that may be relevant to the examination of claims to the present invention. However, it is respectfully submitted that none of the above-indicated patents disclose, teach, suggest, show, or otherwise render obvious, either singly or when considered in combination, the invention described and claimed herein.

SUMMARY OF THE INVENTION

The present invention provides an improved method and apparatus for the administration of alcohol to a person, and therapeutic treatments utilizing the method and apparatus. The method and apparatus of the present invention provides an alcohol "patch" in the form of an adhesive patch or bandage-like structure bearing a quantity of alcohol for transdermal delivery to the user. Permeation enhancers, either chemical or structural, may be included to facilitate the penetration of the alcohol through the skin, and for increased efficacy of delivery of the alcohol to the bloodstream of the user.

The alcohol to be delivered to the user via the inventive apparatus may be plain ethyl alcohol (ethanol) of any suitable concentration or proof, such as neutral grain spirit or pure grain alcohol in 190 proof (95% alcohol). Alternatively, the alcohol may be in the form of various distilled or undistilled spirits (e.g., vodka, gin, rum, whiskey, tequila, and the like), again in suitable proof.

The transdermal patch is designed to deliver a regulated dose of alcohol through the skin and into the bloodstream of the user. The adhesive patch can be applied to the skin of the user on the arm, shoulder, leg, or other body part. Once through the skin, the alcohol easily penetrates the blood vessels and is distributed throughout the body. Once in the bloodstream, the person experiences the same euphoric effects as when an alcoholic beverage is consumed and the alcohol is ingested through the stomach. Generally, the effects of the alcohol begin within 30 to 45 minutes after the patch is applied, with the effects of a single patch lasting up to four hours or longer.

Typically, a person who desires to achieve the effects of drinking an alcoholic beverage must physically consume an alcoholic beverage. Unfortunately, this is not always convenient or socially acceptable. Use of the inventive transdermal patch produces the same effect as ingesting liquor. The inventive patch is convenient, can be carried anywhere, requires no refrigeration, and can be used discreetly and privately.

The transdermal patch may be used by those who don't necessarily enjoy the taste of liquor, but nonetheless desire the effects. Use of the patch may be healthier than ingesting liquor through the stomach, as the alcohol enters directly into the bloodstream, and avoids any ill effects to the user's stomach. In addition, when plain ethyl alcohol is used in the patch, the alcohol contains far fewer impurities than with the use of traditional liquors.

Many people that drink liquor will find a recreational use for the inventive transdermal patch, as described above. The inventive patch may also be utilized in a variety of other applications and therapeutic treatments, including but not limited to:

Therapeutic Treatment of Type II Diabetes:

Type II Diabetes may be controllable in some patients by diet and medication, such that insulin injections may not be required. However, some of these patients find the side effects of the common medications used to be problematic. Although it is widely believed that ethyl alcohol is a carbohydrate and therefore the body reacts to alcohol like any other carbohydrate, the inventors have determined that the body may treat ethyl alcohol as a toxin and may shut down the metabolizing of carbohydrates until the alcohol is out of the system, thereby temporarily lowering a person's blood glucose level. Thus, the inventive alcohol patch may be applied as a therapeutic treatment to reduce the user's blood glucose level. In one example, a subject consumed a sandwich, such that the carbohydrates in the bread caused the subject's blood glucose increase to 200 mg/dL, well over the safe limit of 160 mg/dL. Within 30 minutes of applying the inventive alcohol patch the subject's blood glucose level dropped 40 to 60 points (mg/dL), returning the subject to the "safe" range, and maintained that level for several hours or until the patch was removed.

Alcohol Patches for Use During Medically Monitored Alcohol Detoxification:

Many alcohol treatment programs use a regulated dosage of ethyl alcohol during detoxification to prevent side effects from alcohol withdrawal. The inventive alcohol patch provides a very convenient way to administer a well-controlled dosage of ethyl alcohol, and is far less intrusive than ethyl alcohol injected intravenously (IV). Thus, the inventive patch may be used in the medical field as a delivery system useful for alcohol detoxification, as the timing of administration and the quantity of alcohol can be regulated.

Alcohol Patches for Use as a Hangover Medication:

The inventive alcohol patch has also been determined to be effective in mitigating hangover (alcohol withdrawal) symptoms. Application of the alcohol patch allows a more controlled return to normal. In addition, treatment utilizing the alcohol patch is preferable to traditional "hair of the dog" consumption of alcohol because the alcohol is not on the user's breath, and the patch is inconspicuous.

It is therefore an object of the present invention to provide a new and improved method and apparatus for the administration of alcohol to a person.

It is another object of the present invention to provide a new and improved method and apparatus for the delivery of plain ethyl alcohol (ethanol) of any suitable quantity, concentration or proof to a user.

A further object or feature of the present invention is a new and improved method and apparatus to deliver alcohol to a person who desires to achieve the effects of drinking an alcoholic beverage without physically consuming an alcoholic beverage.

It is another object of the present invention to provide a new and improved method and apparatus for the therapeutic treatment of Type II Diabetes.

It is another object of the present invention to provide a new and improved method and apparatus for use during medically monitored alcohol detoxification.

It is another object of the present invention to provide a new and improved method and apparatus for use as a hangover medication.

Other novel features which are characteristic of the invention, as to organization and method of operation, together with further objects and advantages thereof will be better understood from the following description considered in connection with the accompanying drawings, in which preferred embodiments of the invention are illustrated by way of example. It is to be expressly understood, however, that the drawings are for illustration and description only and are not intended as a definition of the limits of the invention. The various features of novelty which characterize the invention are pointed out with particularity in the claims annexed to and forming part of this disclosure. The invention resides not in any one of these features taken alone, but rather in the particular combination of all of its structures for the functions specified.

There has thus been broadly outlined the more important features of the invention in order that the detailed description thereof that follows may be better understood, and in order that the present contribution to the art may be better appreciated. There are, of course, additional features of the invention that will be described hereinafter and which will form additional subject matter of the claims appended hereto. Those skilled in the art will appreciate that the conception upon which this disclosure is based readily may be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the Abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The Abstract is neither intended to define the invention of this application, which is measured by the claims, nor is it intended to be limiting as to the scope of the invention in any way.

Certain terminology and derivations thereof may be used in the following description for convenience in reference only, and will not be limiting. For example, words such as "upward," "downward," "left," and "right" would refer to directions in the drawings to which reference is made unless otherwise stated. Similarly, words such as "inward" and "outward" would refer to directions toward and away from, respectively, the geometric center of a device or area and designated parts thereof. References in the singular tense include the plural, and vice versa, unless otherwise noted.

BRIEF DESCRIPTION OF THE DRAWINGS

The invention will be better understood and objects other than those set forth above will become apparent when consideration is given to the following detailed description thereof. Such description makes reference to the annexed drawing wherein:

FIG. 1 is a side elevation cross-sectional view of a transdermal patch for alcohol administration of this invention.

DETAILED DESCRIPTION OF THE INVENTION

FIG. 1 illustrates a first preferred embodiment of a transdermal bandage or patch 10 for the administration of alcohol to a user, preferably including a backing layer 12, alcohol reservoir 14, release membrane 16, and contact adhesive layer 18. Backing layer 12 is preferably constructed of a flexible plastic, polymer, or other suitable material that is impermeable to alcohol, completely covers the alcohol reservoir 14, and may be clear, translucent, opaque or colored. Alcohol reservoir 14 may be a simple void or cavity between the backing layer 12 and release membrane 16, or may include a pad of preferably nonwoven material such as nylon, rayon, cotton, or other material that is absorbent and will contain the liquid alcohol prior to use and yet permit delivery of the alcohol when the patch 10 is applied to the skin of the user. The quantity of alcohol contained in the reservoir 14 for delivery to the user can of course vary, but may be in a dose of two grams or more. Release membrane 16 may be constructed of nylon, polymer, thermoplastic fluoropolymer such as pvdf, nitro cellulose, or other suitable material that prevents the free flow and loss of the alcohol prior to the application of the patch 10 to the user's skin, but permits passage and delivery of the alcohol from the reservoir 14 to and through the exposed skin S of the user when applied. Contact adhesive layer 18 surrounds the release membrane 16 and forms a seal with the skin S to prevent leakage of alcohol from around the periphery of release membrane 16. The contact adhesive may be a pressure sensitive water based or solvent based acrylic or silicone adhesive, or other suitable adhesive that will at least temporarily hold the patch structure in place on the user's skin when applied, and yet be selectively releasable from the skin when desired, as when the quantity of alcohol from the patch has been completely delivered to the user through the skin. The entire transdermal patch structure 10 is preferably packaged in an easily opened sealed envelope or other package for the convenience of the user.

Accordingly, the present invention may be characterized as a method for administering a quantity of ethyl alcohol to a subject comprising: providing an adhesive patch structure having a backing layer, an alcohol reservoir bearing a quantity of ethyl alcohol, a release membrane, and a contact adhesive layer; and applying the adhesive patch structure to the skin of the subject for transdermal delivery of the ethyl alcohol through the skin and into the bloodstream of the subject.

Another embodiment of the present invention may be characterized as a method for the therapeutic treatment of Type II Diabetes in a subject comprising: administering a quantity of ethyl alcohol to the subject by providing an adhesive patch structure having a backing layer, an alcohol reservoir bearing a quantity of ethyl alcohol, a release membrane, and a contact adhesive layer; and applying the adhesive patch structure to the skin of the subject for transdermal delivery of the ethyl alcohol through the skin and into the bloodstream of the subject to lower the blood glucose level of the subject.

A further embodiment of the present invention may be characterized as a method for the therapeutic alcohol detoxification of a subject comprising: administering a quantity of ethyl alcohol to the subject by providing an adhesive patch structure having a backing layer, an alcohol reservoir bearing a quantity of ethyl alcohol, a release membrane, and a contact adhesive layer; and applying the adhesive patch structure to the skin of the subject for transdermal delivery of the ethyl alcohol through the skin and into the bloodstream of the subject to provide a regulated dose of ethyl alcohol to the subject.

The above disclosure is sufficient to enable one of ordinary skill in the art to practice the invention, and provides the best mode of practicing the invention presently contemplated by the inventor. While there is provided herein a full and complete disclosure of the preferred embodiments of this invention, it is not desired to limit the invention to the exact construction, dimensional relationships, and operation shown and described. Various modifications, alternative constructions, changes and equivalents will readily occur to those skilled in the art and may be employed, as suitable, without departing from the true spirit and scope of the invention. Such changes might involve alternative materials, components, structural arrangements, sizes, shapes, forms, functions, operational features or the like.

Therefore, the above description and illustrations should not be construed as limiting the scope of the invention, which is defined by the appended claims.

What is claimed as invention is:

1. A method for administering an effective amount of ethyl alcohol to provide the effects of drinking an alcoholic beverage by a subject, the method comprising:
    administering a regulated dose of ethyl alcohol to the subject in a quantity sufficient to affect the subject by providing an adhesive patch structure having a backing layer comprising a flexible material that is impermeable to alcohol, a release membrane, an alcohol reservoir comprising a cavity between the backing layer and the release membrane and completely covered by the backing layer, and bearing at least two grams of ethyl alcohol, and a contact adhesive layer; and
    applying the adhesive patch structure to the skin of the subject for transdermal delivery of the ethyl alcohol through the skin and into the bloodstream of the subject to provide a regulated dose of ethyl alcohol in an effective amount to provide the effects of drinking an alcoholic beverage.

2. A method for mitigating the side effects of alcohol withdrawal, the method comprising:
    administering a regulated close of ethyl alcohol to a subject in a quantity sufficient to affect the subject by providing an adhesive patch structure having a backing layer comprising a flexible material that is impermeable to alcohol, a release membrane, an alcohol reservoir comprising, a cavity between the backing layer and the release membrane and completely covered by the backing layer, and bearing at least two grams of ethyl alcohol, and a contact adhesive layer; and
    applying the adhesive patch structure to the skin of the subject for transdermal delivery of the ethyl alcohol through the skin and into the bloodstream of the subject to provide a regulated dose of ethyl alcohol to mitigate the side effects of alcohol withdrawal.

3. The method of claim 1 or 2 comprising removing the adhesive patch structure from the skin of the subject when the ethyl alcohol from the patch has been completely delivered to the subject.

4. The method of claim 1 or 2 wherein the alcohol reservoir comprises a pad of material that is absorbent and contains the ethyl alcohol prior to use and permits delivery of the ethyl alcohol when the adhesive patch is applied to the skin of the subject.

5. The method of claim 1 or 2 wherein the release membrane is constructed of a material that prevents the free flow and loss of the ethyl alcohol prior to the application of the patch to the subject's skin, but permits passage and delivery of the ethyl alcohol from the alcohol reservoir to and through the skin of the subject when applied.

6. A method for the therapeutic treatment of Type II Diabetes in a subject, the method comprising:

administering a regulated dose of ethyl alcohol to the subject in a quantity sufficient to affect the blood glucose level of the subject by providing an adhesive patch structure having a backing layer, an alcohol reservoir comprising at least two grams of ethyl alcohol, a release membrane, and a contact adhesive layer; and applying the adhesive patch structure to the skin of the subject for transdermal delivery of the ethyl alcohol through the skin and into the bloodstream of the subject to lower the blood glucose level of the subject.

7. A method for the therapeutic alcohol detoxification of a subject, the method comprising:

administering a regulated dose of ethyl alcohol to the subject in a quantity sufficient to affect the subject by providing an adhesive patch structure having a backing layer, an alcohol reservoir comprising at least two grams of ethyl alcohol, a release membrane, and a contact adhesive layer; and applying the adhesive patch structure to the skin of the subject for transdermal delivery of the ethyl alcohol through the skin and into the bloodstream of the subject to provide a regulated dose of ethyl alcohol to the subject to facilitate alcohol detoxification of the subject.

\* \* \* \* \*